(12) United States Patent
Abu Nassar (10) Patent No.: US 10,092,694 B2
(45) Date of Patent: *Oct. 9, 2018

(54) SELECTIVELY IMPLEMENTABLE MULTI-PROBE MICRODRIVE

(71) Applicant: Nabil J. Abu Nassar, Nazareth (IL)

(72) Inventor: Nabil J. Abu Nassar, Nazareth (IL)

( * ) Notice: Subject to any disclaimer, the term of this patent is extended or adjusted under 35 U.S.C. 154(b) by 516 days.

This patent is subject to a terminal disclaimer.

(21) Appl. No.: 14/664,479

(22) Filed: Mar. 20, 2015

(65) Prior Publication Data

US 2015/0265312 A1    Sep. 24, 2015

Related U.S. Application Data

(60) Provisional application No. 61/968,686, filed on Mar. 21, 2014.

(51) Int. Cl.
| | | |
|---|---|---|
| *A61M 5/158* | (2006.01) | |
| *A61N 1/05* | (2006.01) | |
| *A61B 5/00* | (2006.01) | |
| *A61B 90/11* | (2016.01) | |
| *A61B 5/0478* | (2006.01) | |
| *A61B 17/34* | (2006.01) | |

(52) U.S. Cl.
CPC .......... *A61M 5/158* (2013.01); *A61B 5/6868* (2013.01); *A61B 90/11* (2016.02); *A61N 1/0529* (2013.01); *A61B 5/0478* (2013.01); *A61B 2017/3409* (2013.01); *A61B 2560/063* (2013.01); *A61M 2005/1585* (2013.01)

(58) Field of Classification Search
CPC .......... A61M 5/158; A61M 2005/1585; A61B 90/11; A61B 5/6868; A61B 5/0478; A61B 5/0084; A61B 5/04001; A61B 2017/3409; A61B 2017/00367; A61B 2560/063; A61B 17/3468; A61B 17/3415; A61N 1/0529

See application file for complete search history.

(56) References Cited

U.S. PATENT DOCUMENTS

| | | | | |
|---|---|---|---|---|
| 5,643,286 | A * | 7/1997 | Warner | .......... A61B 90/11 604/116 |
| 5,928,143 | A * | 7/1999 | McNaughton | ..... A61B 5/04001 600/373 |
| 6,249,691 | B1 | 6/2001 | Pezaris et al. | |

(Continued)

FOREIGN PATENT DOCUMENTS

WO    WO2009032838 A1    3/2009

OTHER PUBLICATIONS

Altah M. Nichols et al., A screw microdrive for adjustable chronic unit recording in monkeys, Journal of Neuroscience Methods 81 (1998) 185-188.

(Continued)

*Primary Examiner* — Jocelin Tanner
(74) *Attorney, Agent, or Firm* — Guy Levi; The IP Law Firm of Guy Levi, LLC (57) ABSTRACT

The disclosure relates to a selectively and concurrently implementable multi-probe microdrive apparatus. Specifically, the disclosure relates to an apparatus configured to selectively and reversibly couple and/or decouple at least one holder to, and/or from an actuator independently, wherein the actuator is configured for controllably and concurrently move any coupled holder. The holder adapted to have a stimulating and/or recording electrode coupled thereon.

20 Claims, 6 Drawing Sheets

(56) References Cited

U.S. PATENT DOCUMENTS

| | | | | |
|---|---|---|---|---|
| 7,769,421 | B1 | 8/2010 | Stengel et al. | |
| 2002/0120216 | A1* | 8/2002 | Fritz | A61B 5/15146 600/583 |
| 2004/0034318 | A1* | 2/2004 | Fritz | A61B 5/15186 604/19 |
| 2006/0052723 | A1* | 3/2006 | Roe | A61B 5/14514 600/583 |
| 2008/0275466 | A1* | 11/2008 | Skakoon | A61B 17/3417 606/130 |
| 2009/0105776 | A1* | 4/2009 | Aldridge | A61B 5/04001 607/2 |
| 2012/0253361 | A1* | 10/2012 | Drstvensek | A61B 34/72 606/130 |

OTHER PUBLICATIONS

Timothy M. Otchy et al., Design and Assembly of an Ultra-light Motorized Microdrive for Chronic Neural Recordings in Small Animals, JOVE http://www.jove.com/video/4314.
VersaDrive4, Construction Instructions Nuralynx.
Tetrode Screw Drive (TSD-2-VV), Thomas Recording GmbH.

* cited by examiner

SELECTIVELY IMPLEMENTABLE MULTI-PROBE MICRODRIVE

RELATED APPLICATIONS

This application claims priority benefit of U.S. Provisional Application Ser. No. 61/968,686, filed Mar. 21, 2014, the contents of which are hereby incorporated by references.

BACKGROUND

The disclosure is directed to a selectively and concurrently implementable multi-probe microdrive apparatus. Specifically, the disclosure is directed to an apparatus configured to selectively and reversibly couple and/or decouple at least one holder to, and/or from an actuator independently, wherein the actuator is configured for slectably controllably and concurrently moves any coupled holder.

In recent years, recording neuronal activity in the brain of awake, behaving animals has become a major tool in behavioral electrophysiology. Neural recording or targeted electrical stimulation and the like, typically selects different parts of the brain, often at different depths from the skull to obtain different information. One approach to contacting the target area involves trans-cranial (or extra-cellular, in the case of biological tissue samples) electrode insertion. Trans-cranial (or extra-cellular) electrode insertion typically involves the insertion of one or more electrodes into the tissue. Conventional trans-cranial electrode insertion has traditionally followed one of two paths; chronic (long-term) or acute (typically, less than one day).

The positioning of the electrodes is important for reaching a specific target in the brain for diagnostic, research and healing purposes, e.g. for extra cellular or trans-cranial recording from the brain and the nervous system as well as in functional neurosurgery or other biological tissue samples. Such electrode positioning devices although known, consist essentially of a base or an adapter, for positioning the electrodes in the XY plane as well as a discrete, system for positioning the electrodes in the Z plane independently and sequentially.

Accordingly, there is a need for a positioning system capable of positioning probes (e.g., electrodes) in a concurrent manner, without compromising the flexibility of adjusting depth discretely and in a predetermined lay-out.

SUMMARY

In an embodiment, provided is a drive device for contacting at least one probe with a biological sample, the device comprising: at least one holder operably coupled to at least one probe having a predetermined function; at least one selector configured to selectively and reversibly couple and/or decouple said at least one holder to, and/or from an actuator independently, wherein, said actuator is configured for controllably and concurrently move any coupled holder.

In another embodiment, provided herein is a method for contacting at least one probe with a biological tissue sample comprising: exposing the biological tissue sample; providing a device comprising: at least one holder operably coupled to at least one probe having a predetermined function; and at least one selector configured to selectively and reversibly couple and/or decouple said at least one holder to, and/or from an actuator independently, wherein, said actuator is configured for controllably and concurrently move any coupled holder; positioning the device such that the probe will contact an area of interest in the biological tissue sample; coupling at least one probe to the actuator; activating the actuator, contacting the biological sample; and decoupling the at least one probe from the actuator.

BRIEF DESCRIPTION OF THE DRAWINGS

The features of the selectively and concurrently implementable multi-probe microdrive apparatus described herein will become apparent from the following detailed description when read in conjunction with the drawings, which are exemplary, not limiting, and wherein like elements are numbered alike in several figures and in which.

While the disclosure is amenable to various modifications and alternative forms, specifics thereof have been shown by way of example in the drawings and will be further described in detail hereinbelow. It should be understood, however, that the intention is not to limit the disclosure to the particular embodiments described. On the contrary, the intention is to cover all modifications, equivalents, and alternatives.

DETAILED DESCRIPTION

The disclosure relates in one embodiment to selectively and concurrently implementable multi-probe microdrive apparatus. In another embodiment, the disclosure relates to devices configured to selectively and reversibly couple and/or decouple at least one holder to, and/or from an actuator independently, wherein the actuator is configured for controllably and concurrently move any coupled holder.

Detailed embodiments of the present technology are disclosed herein; however, it is to be understood that the disclosed embodiments are merely exemplary, which can be embodied in various forms. Therefore, specific structural and functional details disclosed herein are not to be interpreted as limiting but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the probe(s) includes one or more probe). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

In addition, for the purposes of the present disclosure, directional or positional terms such as "top", "bottom", "upper," "lower," "side," "front," "frontal," "forward," "rear," "rearward," "back," "trailing," "above," "below," "left," "right," "horizontal," "vertical," "upward," "downward," "outer," "inner," "exterior," "interior," "intermediate," etc., are merely used for convenience in describing the various embodiments of the present disclosure.

In an embodiment, provided herein is a drive device for contacting at least one probe with a biological sample, the device comprising at least one holder operably coupled to at least one probe having a predetermined function; at least one selector configured to selectively and reversibly couple and/or decouple said at least one holder to, and/or from an actuator independently, wherein, said actuator is configured for controllably and concurrently move any coupled holder. The term "selectively" is used in the disclosure or the claims, is intended to refer to a condition of a component wherein a user of the apparatus may activate or deactivate the feature or function of the component as is necessary or desired in use of the apparatus. The activation or deactivation can occur for example, without affecting the condition, feature or function of other components of the apparatus.

The actuator used in the selectively and concurrently implementable multi-probe microdrive apparatus described herein can be a screw gear, which can be positioned axially in a cartridge containing the holder(s) and selector(s) described herein. The term actuator refers to any of a number of actuation devices which may be utilized in articulating various members and linkages in the selectively and concurrently implementable multi-probe microdrive apparatus described herein. For example, the actuator can be a screw drive, adapted to rotate clock-wise (CW) and counter-clockwise (CCW), such that CW rotation will lower the probe(s), while CCW rotation will elevate any engaged holder. Likewise, the actuator can be a rotating sleeve (see e.g., FIG. 3B), having an interior threading configured to engage the holder. The actuator may be turned manually or be motorized, or be adapted to couple to a drive shaft. The threading on the screw gear actuator may cover substantial axial length of the screw gear, for example between about 50% and about 100% of the axial length.

The selector used in the selectively and concurrently implementable multi-probe microdrive apparatus described herein can selectively (e.g., as needed without affecting overall operation of the device) couple, decouple or both, the holder to the actuator or from the actuator at any position along a longitudinal axis length. In other words, when desired or required several holders can be coupled to the actuator and be lowered or elevated simultaneously and concurrently to a desired point, then each engaged holder can be discretely decoupled by, for example moving the selector to disengage the holder. The action can be reversible, in other words, engaging or disengaging (or coupling and decoupling) can take place without adversely affecting any of the components involved and can take place at any point along the axial length (i.e., the longitudinal axis length of the actuator). Likewise, elevating the probes coupled to the holders can be done simultaneously and concurrently by selecting the probes sought to be elevated concurrently, using the appropriate selector, coupling the holder to the actuator and elevating the probe. The selector may be a mechanical selector requiring user intervention by rotating a nut having an off center bore therein such that a rotation of the nut will cause a support rod engaged in the bore to move radially. In another embodiment, the selector can be a magnetic selector, configured to have the holder engage either the actuator or the wall opposite the actuator.

The holder used in the selectively and concurrently implementable multi-probe microdrive apparatus described herein can be a monolithic truck having defined therein at least one bore adapted to slidably receive a support rod. As used herein the term "slidably coupled" and the term "slidably attached" is defined in one embodiment by the attachment or connection of two components such that the pieces are pressure-fit together. "Pressure-fit," is a term known to those skilled in the art. The term can refer to a bond caused by mutual pressure acting on the contact surfaces between two parts in contact, wherein the two parts require no weld, screw, or nail connection, which allows movement of one component in relation to the other. In another embodiment, term "slidably coupled" or derivatives thereof refers to a state in which two or more components are coupled to one another in which at least one of the components at least slides with respect to another component. The terms "slide," "slid" or "sliding" are defined as moving, gliding or passing along a surface, although continuous contact is not necessarily required.

Accordingly and in an embodiment, the holder can be slidably coupled to a support rod, flanked at the proximal end and distal end with nuts, such that when engaged on the actuator, the threading on the actuator (when present) engages complimentary threading on the holder wall, while when not engaged by the actuator, the holder wall opposite the wall engaging the actuator is frictionally coupled to the housing cap in one embodiment (e.g., an axial actuator), or (frictionally coupled) to a central wall in another embodiment (e.g., radial actuator). Alternative coupling can also be done using magnets.

The holder can have, for example a slab shape with a narrow frame having at least one plane that is complimentary threaded to the screw drive actuator, or the internally threaded sleeve actuator. Alternatively, the holder used in the selectively and concurrently implementable multi-probe microdrive apparatus described herein can be a hybrid holder (in other words, non-monolithic having several parts operably coupled to each other, forming enhanced functionality) that further comprise an engaging holder member adapted to engage the actuator. The engaging holder member can be slidably coupled to a stationary holder member (e.g., using a rail and channel configuration), which is incapable of engaging the actuator (in other words, there is no interface that can come in contact with the actuator and be engaged), the engaging holder member can have a support rod bore that has an oval cross section. Having the oval cross section can be configured to facilitate coupling or decoupling of the engaging holder member from the actuator without substantially creating strain along the X direction on the support rod of the selector, thus reducing the risk of unintentionally changing the positioning of the probe in the biological tissue sample. Likewise the stationary holder member can be configured to be radially immobile, in other words, the position of the stationary holder member along the X axis remains constant throughout the operation of the drive. In addition the engaging holder member can be further partitioned to an engaging member and a tuning member, which can provide fine tuning at the contact point and have different thread pitch than for example, the screw gear actuator (when a screw gear is used). The tuning holder member can be operably coupled to the engaging holder member to provide the proper tuning along the Z axis. The engaging and tuner holder member can each be motorized or be powered separately. For example, servo motors can be attached to each selector or to the tuning holder member.

The probe(s) used in the selectively and concurrently implementable multi-probe microdrive apparatus described herein can be, for example a cannula, an electrode, a tetrode, a needle, a sensor, fiber optic, fiber-optogenic (FOG) stimulator, a pipette, or a combination comprising one or more of the foregoing. For example, a cannula can be used to provide a targeted drug delivery to, or near a specific neuron cluster, for example, targeted delivery of monoclonal antibodies to dissolve beta-amyloid brain plaque. Likewise, electrodes can be used for targeted elctrostimulation or tetrodes (or any number n' of coiled data recording probes) can be used to collect data. The probes can be used to achieve a predetermined function, for example, data collection, stimulation, sensing, drug delivery or a combination of function and/or features comprising one or more of the foregoing. For example, fine wire electrodes can be used for chronic and acute recordings in freely moving animals using the devices described herein. This method allows stable recordings for a long time. However, fine wire electrodes have low selectivity and typically record the activity of a large number of cells. To increase the selectivity, two (stereotrode) or four (tetrode) wires can be coiled together to provide multichannel recording of the same neuron cluster. Analysis of recordings on the basis of temporal coherence of spikes across channels can be done off-line for single unit sorting. Tetrode probes used in the devices described herein can provide both stability and selectivity of recordings.

For example, the electrodes may extend in the lengthwise direction. First end surfaces of the electrodes may be exposed to measure bio-signals. Likewise, the tetrode may precisely detect locations from which the bio-signals are transmitted. In other words, a particular neuron from which a bio-signal is transmitted may be known precisely. Therefore, the tetrode may easily and precisely perform single unit recording. Furthermore, second end surfaces of the electrodes may be connected to an electrical circuit, so that the bio-signals input by the electrodes may be analyzed. Therefore, the tetrode may be used in various fields of brain research, such as brain computer interface (BCI), deep brain stimulation (DBS), etc.

The probe(s) used in the selectively (in other words, activating and deactivating the probes can be done without affecting other probes), and concurrently implementable multi-probe microdrive apparatus described herein can be used for stimulation. A stimulus can be applied to a neural system in order to elicit a response from it. The term "applied" indicates that the stimulus is administered or delivered to the system in such a way that it reacts to it with a measurable response. The stimulus can be applied directly to the same loci where the response is measured, or it can be applied remotely at a distance from it. For instance, stimulus can be applied on one side of a neural system (e.g., a brain), and then the response to it measured contralaterally. In an embodiment, the probe(s) used in the selectively and concurrently implementable multi-probe microdrive apparatus described herein can be configured for providing a stimulus, as well as for recording responses.

In another example, brain electrical activity can be detected by an electrical detector attached to the selectively and concurrently implementable multi-probe microdrive apparatus described herein, recorded in a memory or other computer readable media of a computer system, and analyzed for extracting information relating to, for example, level of activity. Such an analyzed signal can then be used to generate a response stimulus signal, using, for example, the selectively and concurrently implementable multi-probe microdrive apparatus described herein adapted for generating the response signal, to send an appropriate optimal electrical activation to subcortical structures in the brain involved in forebrain arousal. Alternatively, by way of example and not as a limitation, other forms of detection and stimulation, such as sampled local field potential recordings coupled to a fiber-optogenic (FOG) system or a radio-frequency controlled "BION" system can be used.

The selector used in the selectively and concurrently implementable multi-probe microdrive apparatus described herein can be comprised of a pair of nuts disposed at the axial edges of a support rod adapted to slidably couple to the holder (or engaging holder). The nuts can define a bore therein, wherein the bore is off-center such that, when the nuts are rotatably coupled to the distal support plate and the proximal support plate of the microdrive probe cartridge, rotating the nuts will cause the support rod and by proxy, the holder to move radially and couple to, or decouple from the actuator (see e.g., FIG. 6B). For example, the selector can be rotated 180° to couple and/or decouple the holder to and/or from the actuator. Other configurations are also possible (e.g., using magnets or other angular rotation). The nut disposed within the distal support plate of the Microdrive probe cartridge can further define a visual marker (e.g., a channel, protrusion and the like) marking the position of the holder to the user, indicating whether the holder is engaged or not. When not engaged, the holder can be frictionally or magnetically coupled to a support wall opposite the actuator, thus selectively fixing the holder in the Z direction.

The term "coupled", including its various forms such as "operably coupled", "coupling" or "coupleable", refers to and comprises any direct or indirect, structural coupling, connection or attachment, or adaptation or capability for such a direct or indirect structural or operational coupling, connection or attachment, including integrally formed components and components which are coupled via or through another component or by the forming process (e.g., an electromagnetic field). Indirect coupling may involve coupling through an intermediary member or adhesive, or abutting and otherwise resting against, whether frictionally (e.g., against a housing) or by separate means without any physical connection.

The biological sample for which the selectively and concurrently implementable multi-probe microdrive apparatus described herein can be used, can be for example, an animal's organ, a tissue sample, a slide, cerebral-spinal fluid, a neuron, or brain tissue. The multi-probe devices described herein can have between 2 and about 256 probes (or holders). For example, the selectively and concurrently implementable multi-probe microdrive apparatus described herein can have between 2 and about 128 probes, or between 2 and about 64 probes, specifically, between 2 and about 32 probes, or between 2 and about 16 probes. Configuration can also have 6, 8 or 10 probes therein (see e.g., FIG. 3A). As described herein, each probe selector is capable of selectively coupling and/or decoupling any and all probes' holder(s) to and/or from a single actuator, each at any position along a longitudinal axis length.

In an embodiment, the devices disclosed herein can be used in the methods provided. Accordingly and in an embodiment, provided herein is a method for contacting at least one probe with a biological tissue sample comprising: exposing the biological tissue sample; providing a device comprising: at least one holder operably coupled to at least one probe having a predetermined function; and at least one selector configured to selectively and reversibly couple and/or decouple said at least one holder to, and/or from an actuator independently, wherein, said actuator is configured for controllably and concurrently move any coupled holder; positioning the device such that the probe will contact an area of interest in the biological tissue sample; coupling at least one probe to the actuator; activating the actuator, contacting the biological sample; and decoupling the at least one probe from the actuator. Exposing the biological tissue sample can be for example, by craniotomy, or spinal tap.

The term "engage" and various forms thereof, when used with reference to retention of a member, refer to the application of any forces (e.g., magnetic) that tend to hold two components together against inadvertent or undesired separating forces (e.g., such as may be introduced during use of either component). It is to be understood, however, that engagement does not in all cases require an interlocking connection that is maintained against every conceivable type or magnitude of separating force. Also, "engaging element" or "engaging member" refers to one or a plurality of coupled components, at least one of which is configured for releasably engaging an actuator.

A more complete understanding of the components, processes, assemblies, and devices disclosed herein can be obtained by reference to the accompanying drawings. These figures (also referred to herein as "FIG.") are merely schematic representations (e.g., illustrations) based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 1:
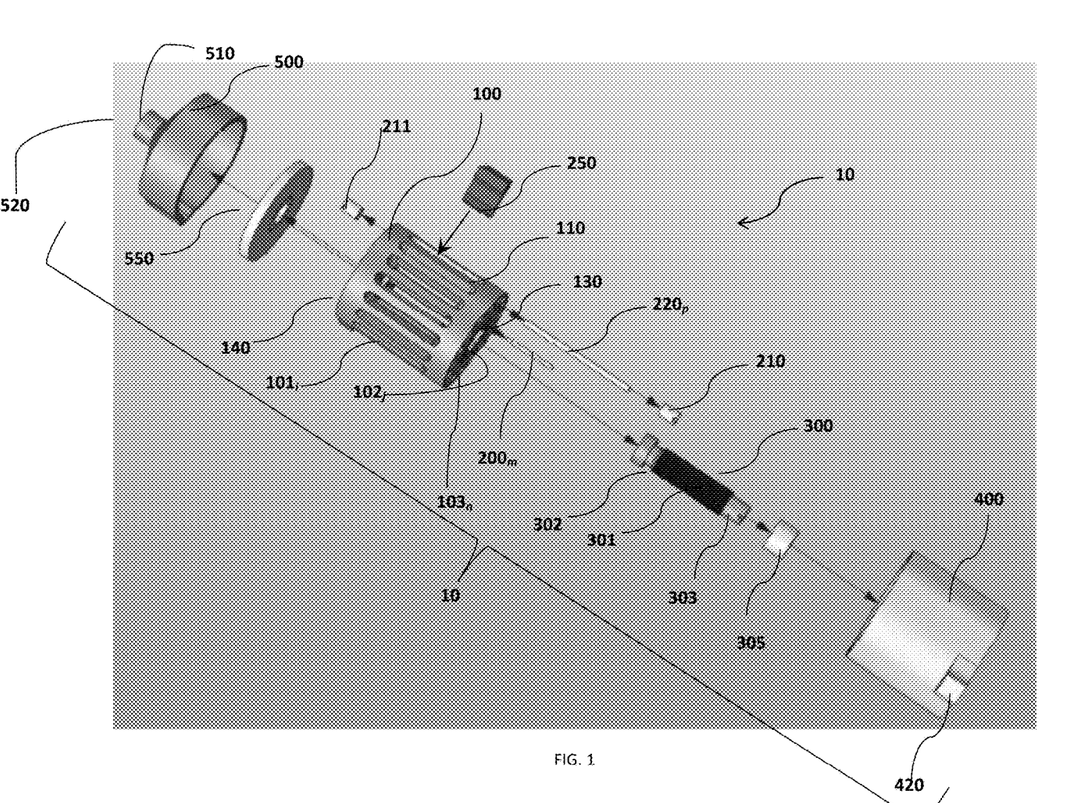
FIG. 1, shows an illustration of an embodiment of an exploded view of the selectively and concurrently implementable multi-probe microdrive apparatus.

Turning now to FIGS. 1-4, where FIG. 1 illustrates an exploded isometric view of the selectively and concurrently implementable multi-probe microdrive apparatus 10 described herein having probe holding cartridge 100, having wall 110 disposed between distal end support plate 130 and proximal end support plate 140 (not shown), the support plates each defining an array of a plurality of apertures axially disposed around the support plates' 130, 140 center in at least two rows ($102_j$ and $103_n$), each row having an equal number of apertures to any other row, wherein each of $j^{th}$ and $n^{th}$ apertures in distal support plate 130 has a corresponding concentric aperture of the diameter on proximal support plate 140. Probe-holding cartridge can further defining plurality of maintenance slots $101_i$ radially disposed in probe-holding cartridge wall 110, each $i^{th}$ maintenance slot $101_i$ being perpendicular to a line defined by any column comprising at least a pair of $j^{th}$ and $n^{th}$ apertures on any of distal and proximal support plates 130, 140 respectively. Also illustrated is actuator 300 having flanged proximal end 302 and distal end 303 with threaded portion 301 therebetween, adapted to convert radial (in other words rotational) motion to an axial motion (in other words linear along the actuator's longitudinal axis), actuator 300 operably coupled to probe-holding cartridge 100, via, for example a central depression in proximal support plate 140 adapted to receive and engage actuator 300 flanged proximal end 302. Likewise, distal end 303 can be operably coupled to distal support plate 130 through a centrally disposed bore adapted to receive and engage actuator 300 distal end 303, which may protrude from distal support plate 130 and be coupled to an additional nut 305 (see e.g., FIG. 2A) configured to attach to an external power source, such as a manual crank or a motor.

Figure 2A:
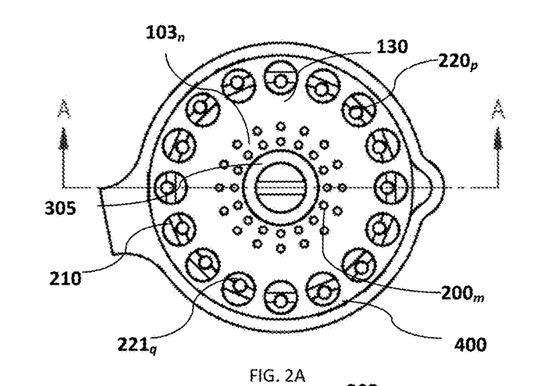
FIG. 2A, shows a top view of an embodiment of the selectively and concurrently implementable multi-probe microdrive apparatus having a central actuator and 16 channels, with FIG. 2B illustrating YZ cross section along cross section line A-A in FIG. 2A showing an engaged and a non-engaged holder position.

Apparatus (or device) 10 further comprises plurality of holders 250 (or carts), each cart or holder defining therein at least pair of bores 253, 252 (see FIG. 4) therein, bores 253, 252 configured to coaxially align with $j^{th}$ and $n^{th}$ apertures in a column of the aperture array $102_j$ and $103_n$ on distal support plate 140 and the corresponding $j^{th}$ and $n^{th}$ apertures in column of proximal end support plate 130 aperture array $102_j$ and $103_n$, each holder 250 adapted to selectively engage actuator 300. As illustrated in FIGS. 2A and 4, holder (or cart) 250 can have a slab shape with a narrow frame having at least one plane 255 that is complimentary to actuator 300, or internally threaded sleeve actuator illustrated in FIG. 3B. Back plane 254 opposite plane 255 is configured to couple to either housing cap 400 (see e.g., FIG. 1), or central column 111 (see e.g., FIG. 3B). Coupling of back plane 254 to housing cap 400 or central column 111 can be frictional by rotating selector nut 210, or by any appropriate means, for example a magnet.

The device can further comprise plurality of support rods $220_p$ (see e.g., FIGS. 1, 2A, 2B, 3A, 3B), each $p^{th}$ support rod 220 slidably coupled to holder 250 through bore 253, each $p^{th}$ support rod 220 extending the length of probe-holding cartridge's 100 axial length. Each $p^{th}$ support rod 220 comprises a portion of selector and is coupled to first nut 210 (see e.g., FIG. 3A), and second nut 211 (see e.g., FIG. 2B) each having an eccentric bore $221_q$ therein, wherein each first nut 210 being rotatably coupled to aperture $102_j$ in distal support plate 130 and each second nut 211 being rotatably coupled to corresponding $j^{th}$ aperture in proximal support plate 140, eccentric bore $221_q$ adapted to receive and engage support rod $220_p$, whereby rotation of first nut 210 through distal support plate 130 (see e.g., FIGS. 2A, 3A) a predetermined number of degrees (e.g., about 180°) selectively causes holder 250 to engage (see FIGS. 2B, 3B) or disengage (see e.g., FIG. 2B) actuator 300.

Device or apparatus 10 further has a plurality of substantially elongated members or probes 200 having a predetermined function, each probe $200_m$ operably coupled to bore 230, each $m^{th}$ probe $200_m$ extending at least beyond proximal support plate 140, through aperture 240 disposed on proximal support plate 140, aligned with holder 250 bore 252.

As illustrated in FIG. 1 housing cap 400 (see e.g., FIGS. 1, 2A, 3A) operably coupled to distal end support plate 130 of probe-holding cartridge 100; and housing base 500, operably coupled to proximal end support plate 140 of probe-holding cartridge, housing base 500 having 510 orifice therein defining channels 515 defined therein, allowing for discrete passage of probes $200_m$, wherein rotation of actuator 300 is adapted to cause selectively engaged holder 250 to move axially. Also illustrated in FIGS. 1, 2B, and 3B is insert 550.

Figure 3A:
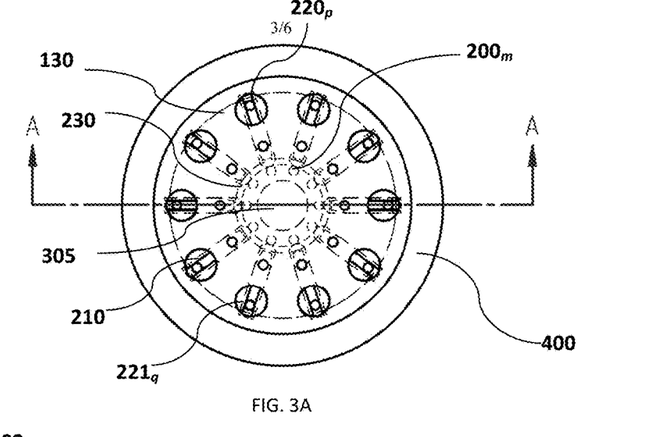
FIG. 3A illustrates a top view of an embodiment of the selectively and concurrently implementable multi-probe microdrive apparatus having a radial actuator and 10 channels, with FIG. 3B illustrating YZ cross section along cross section line A-A in FIG. 3A showing an engaged holder position.
Figure 3B:
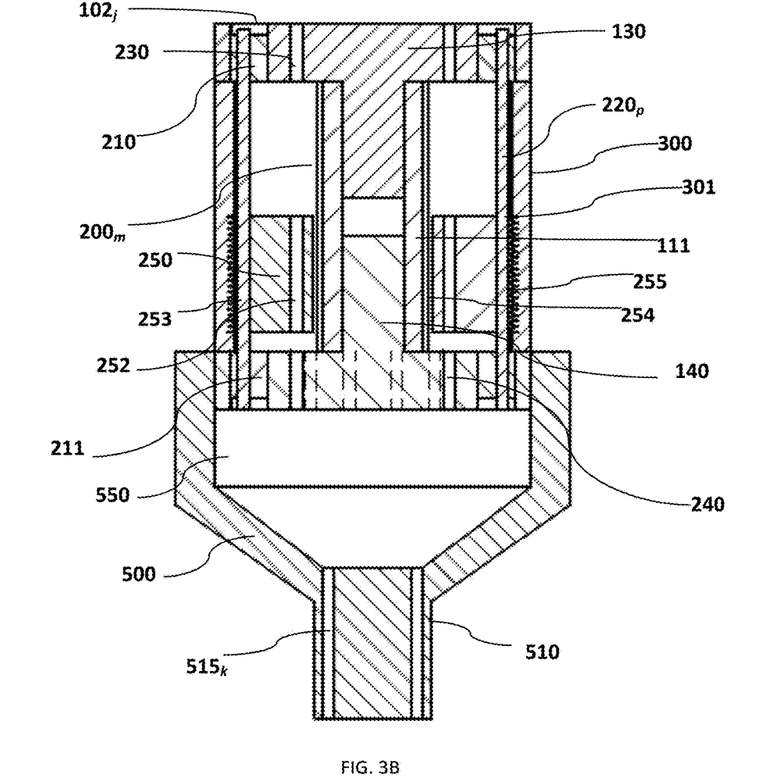
Figure 4:
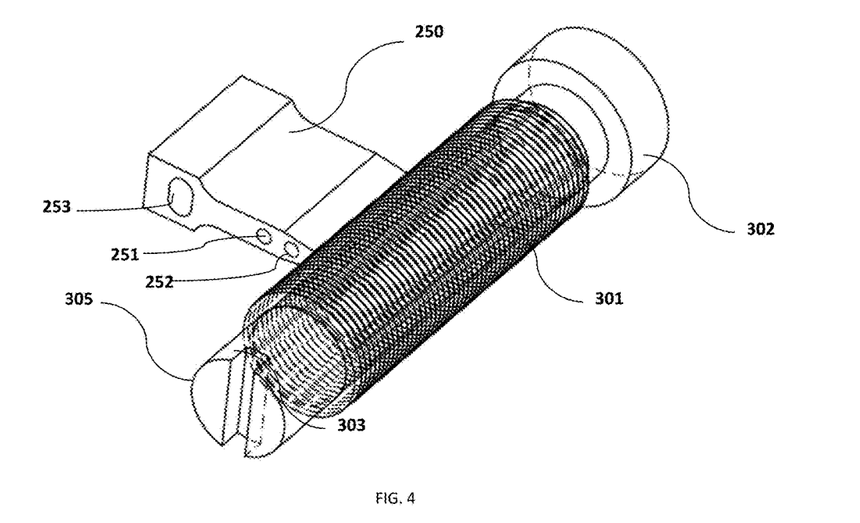
FIG. 4, illustrates an embodiment of an axial screw gear actuator coupled to a monolithic holder.

Turning now to FIG. 3, with a top view of the selectively and concurrently implementable multi-probe microdrive apparatus having a radial actuator (in other words, internally threaded tubular sleeve and 10 channels (FIG. 3A), with FIG. 3B illustrating YZ cross section along cross section line A-A in FIG. 3A showing engaged holder 250 positioned such that engaging plane 255 is radial and closer to support rod $220_p$, than to probe $200_m$. As shown, selectively and concurrently implementable multi-probe microdrive apparatus 10 has probe holding cartridge 100, having wall 110 disposed between distal end support plate 130 and proximal end support plate 140, and central support column 111. Also illustrated is radial actuator 300 having with internally threaded portion 301, adapted to engage complimentary threaded portion 255 of holder 250 and convert radial (in other words rotational) motion to an axial motion (in other words linear along radial actuator's 300 longitudinal axis), actuator 300 operably slidably coupled to probe-holding cartridge 100, via, for example a radial channel defined between proximal support plate 140 and housing cap 400, adapted to receive and engage radial actuator 300. As illustrated, holders 250 defining therein at least pair of bores 253, 252 therein whereby each holder 250 adapted to selectively engage actuator 300. As illustrated in FIG. 3B, holder (or cart) 250 can have a slab shape with a narrow frame having plane 255 that is complimentary to internally threaded sleeve actuator. When not engaged, back plane 254 can be coupled to central support column 111 securing holder 250 along the Z direction of device 10 longitudinal axis.

Figure 5:
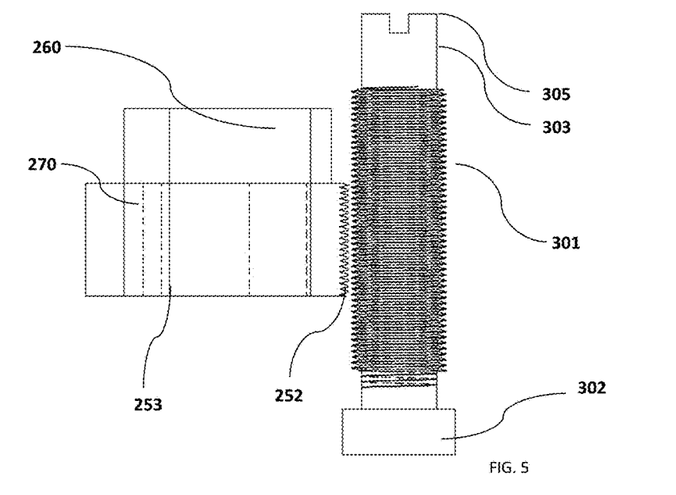
FIG. 5 illustrates another embodiment of the axial screw gear actuator with hybrid holder.

Turning now to FIG. 5, illustrating another embodiment of axial screw gear actuator 300 having flanged proximal end 302 and distal end 303 with threaded portion 301, adapted to convert radial (in other words rotational) motion to an axial motion (in other words linear along the actuator's longitudinal axis), actuator 300 operably coupled to probe-holding cartridge 100 (not shown, see e.g. FIG. 6A), via, for example a central depression in proximal support plate 140 (not shown, see e.g., FIG. 2A) adapted to receive and engage actuator 300 flanged proximal end 302. Likewise, distal end 303 can be operably coupled to distal support plate 130 (not shown, see e.g. FIG. 2A) through a centrally disposed bore adapted to receive and engage actuator 300 distal end 303, which may protrude from distal support plate 130 (not shown, see e.g. FIG. 2A) and be coupled to an additional nut, or define a groove 305 therein, configured to be coupled to an external power source, such as a manual crank or a motor. Also illustrated in FIG. 5, is hybrid (in other words, comprising several parts) holder further comprising engaging holder member 250 adapted to engage actuator 300, slidably coupled to stationary holder member 260 incapable of engaging actuator 300, engaging holder member 250 defining bore 253 adapted to receive and engage support rod $220_p$ (not shown, see e.g. FIG. 2A) and bore 252 adapted to receive and engage probe $200_m$ (not shown, see e.g. FIG. 2B) therein. Bore 253 can have an oval XY cross section, such that rotating nut 210 of the mechanical selector will not cause strain on support rod $220_p$. Also shown is stationary holder 260 member having corresponding bores 263 and 262 respectively (not shown), stationary holder member 260 configured to be radially immobile. Tuning member 270 is also shown, adapted to provide additional motion along the Z direction at predetermined increments.

Figure 2B:
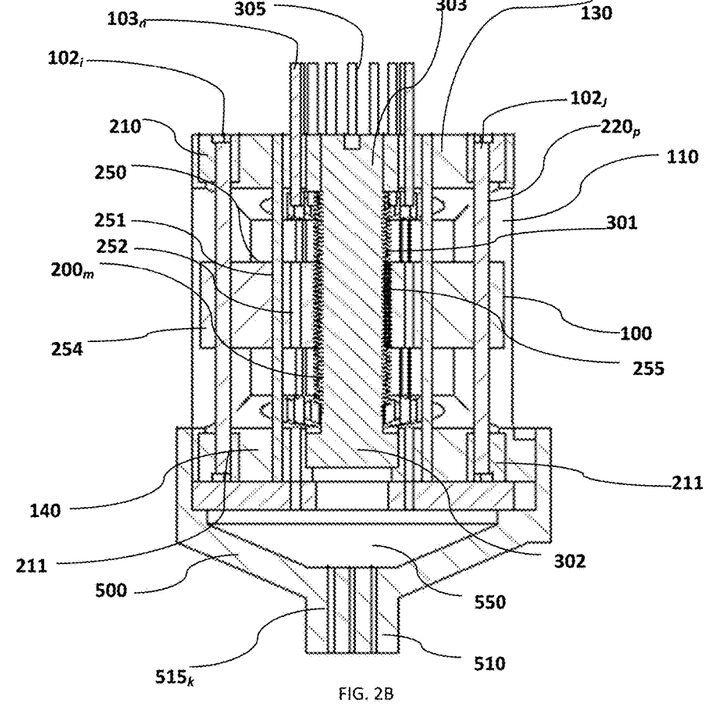
Figure 6A:
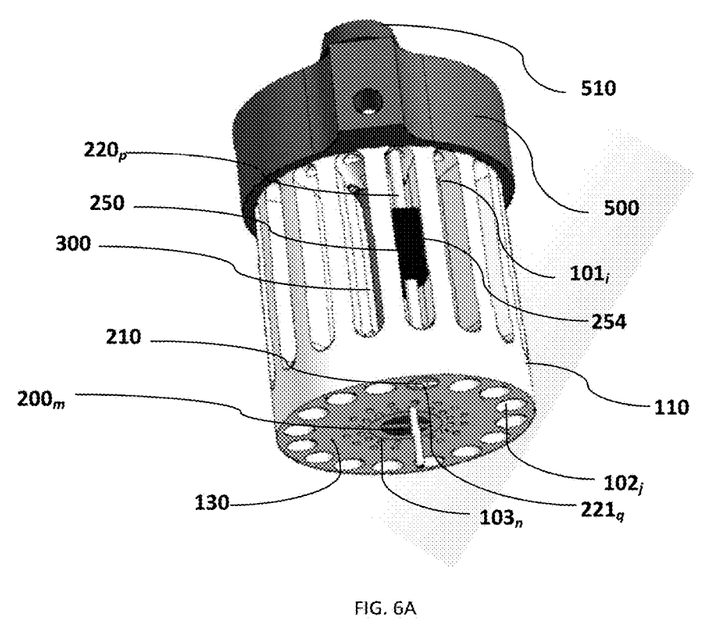
FIG. 6A illustrates an embodiment of a probe holder cartridge, with an embodiment of the selector assembly in FIG. 6B.

Turning now to FIG. 6, illustrating in FIG. 6A an embodiment of a probe holder cartridge, showing probe holding cartridge 100, having wall 110 disposed between distal end support plate 130 (Not shown, see e.g., FIG. 1) and proximal end support plate 140 (not shown, see e.g., FIG. 2B). As illustrated, probe-holding cartridge 100 defines plurality of maintenance slots $101_i$ radially disposed in probe-holding cartridge wall 110. As illustrated, probe holder cartridge further holds holder (or cart) 250 slidably coupled to support rod $220_p$, and back plane 254 configured to be coupled for example to housing cap 400 (not shown, see e.g., FIG. 8) when not engaged to actuator 300 with probe $200_m$ extending beyond proximal end support plate 140 (not shown, see e.g., FIG. 2B).

Figure 6B:
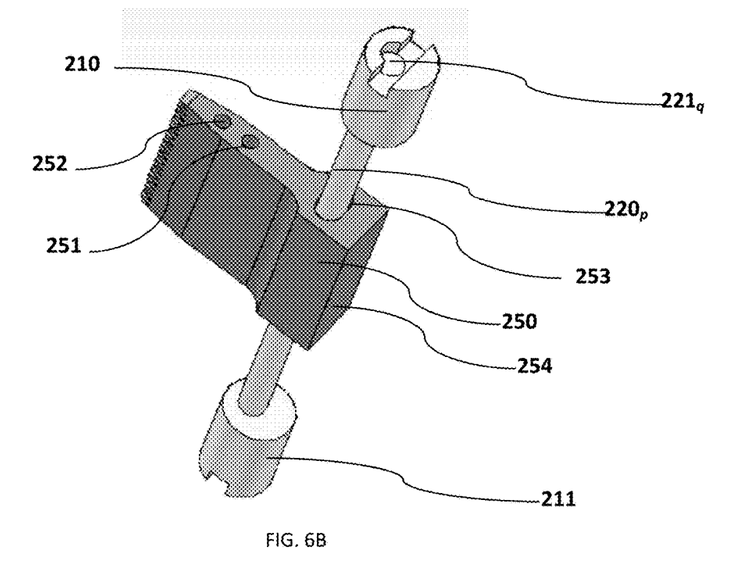

As shown in FIG. 6B, the selector can comprise support rod $220_p$ slidably coupled to holder 250 through bore 253. Bore 253 can have an oval cross section configured to reduce strain and stress on support rod $220_p$. Support rod $220_p$ can extend the length of probe-holding cartridge's 100 axial length (see e.g., FIG. 6A). Each support rod $220_p$ can comprise a portion of selector and is coupled to first nut 210 and second nut 211 each having an eccentric bore $221_q$ therein, wherein each first nut 210 being rotatably coupled to aperture $102_j$ (see e.g., FIG. 6A) in distal support plate 130 and each second nut 211 being rotatably coupled to corresponding $j^{th}$ aperture in proximal support plate 140 (not shown, see e.g., FIG. 2B) eccentric bore $221_q$ adapted to receive and engage support rod $220_p$, whereby rotation of first nut 210 through distal support plate 130 (see e.g., FIGS. 2A, 3A) a predetermined number of degrees (e.g., about 180°) selectively causes holder 250 to engage (see FIGS. 2B, 3B) or disengage (see e.g., FIG. 2B) actuator 300.

Figure 7:
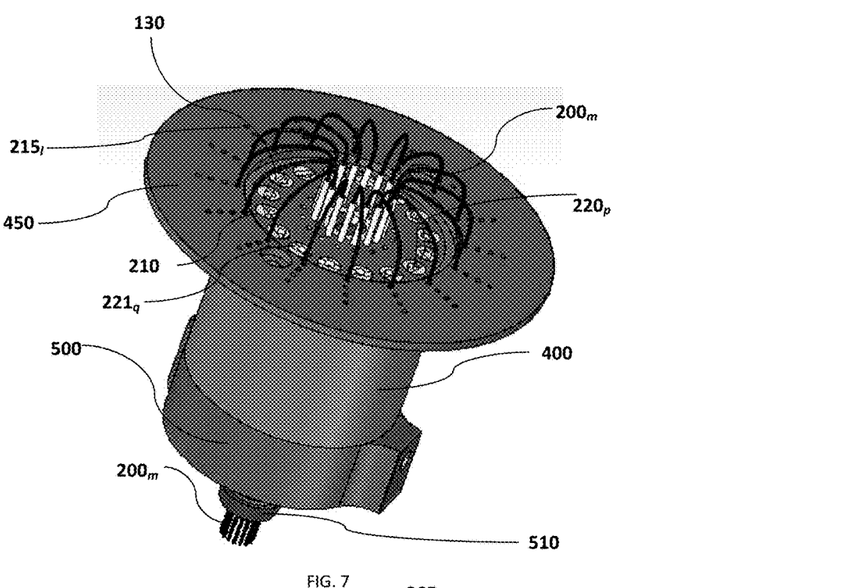
FIG. 7, illustrates an embodiment of the assembled selectively and concurrently implementable multi-probe microdrive apparatus having a plurality of electrode coupled to a printed circuit board (PCB)
Figure 8:
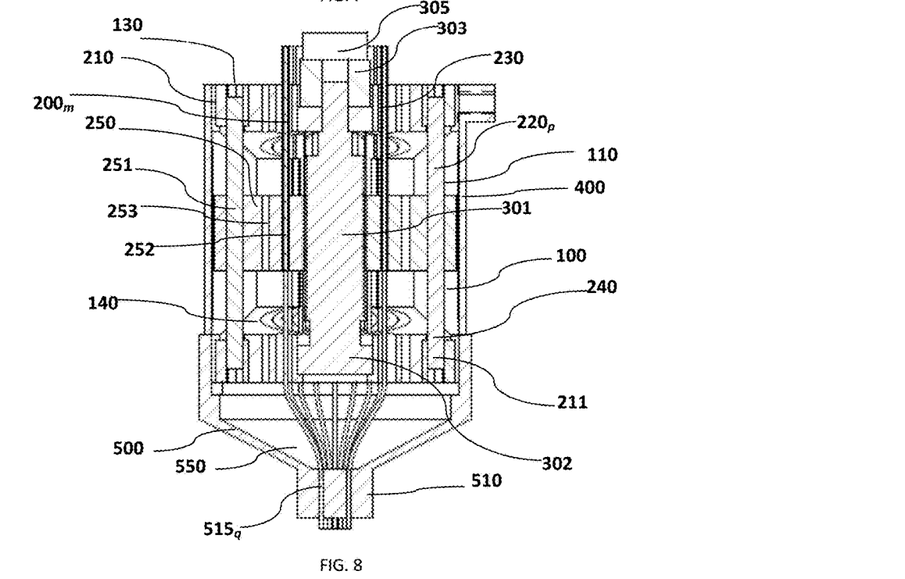
FIG. 8, illustrates a cross-section along the YZ plane of the assembled Microdrive having a plurality of probes.

Turning now to FIGS. 7 and 8, illustrating in FIG. 7 an embodiment of the assembled selectively and concurrently implementable multi-probe microdrive apparatus 10 having a plurality of electrodes $200_m$ extending above printed circuit board (PCB) 450 of housing cap 400 coupled to contact columns $215_l$. As shown, the PCB is configured for accommodating a plurality of, for example, tetrodes where each channel will be coupled (e.g., welded) to the corresponding column. Also shown is housing base 500 having orifice 510 defining therein channels $515_k$ (not shown, see e.g., FIG. 8). It should be noted, that the disclosed devices and methods can be provided such that the probe lay-out on the X-Y plane is customized. Although shown in a single Y-Z plane in FIG. 8, the distances between adjacent probes can be predetermined.

As shown in FIG. 8, selectively and concurrently implementable multi-probe microdrive apparatus 10 has probe holding cartridge 100, having wall 110 disposed between distal end support plate 130 and proximal end support plate 140. Also illustrated is actuator 300 having flanged proximal end 302 and distal end 303 with threaded portion 301 therebetween, adapted to convert radial (in other words rotational) motion to an axial motion (in other words linear along the actuator's longitudinal axis), actuator 300 operably coupled to probe-holding cartridge 100, via, for example a central depression in proximal support plate 140 adapted to receive and engage actuator 300 flanged proximal end 302. Likewise, distal end 303 can be operably coupled to distal support plate 130 through a centrally disposed bore adapted to receive and engage actuator 300 distal end 303, which may protrude from distal support plate 130 and be coupled to an additional nut 305 or groove configured to attach to an external power source, such as a manual crank or a motor.

As shown, device 10 has plurality of support rods 220$_p$, each p$^{th}$ support rod 220 slidably coupled to holder 250 through bore 253, each p$^{th}$ support rod 220$_p$ extending the length of probe-holding cartridge's 100 axial length. Each p$^{th}$ support rod 220$_p$ comprises a portion of selector and is coupled to first nut 210, and second nut 211, wherein each first nut 210 being rotatably coupled to aperture 102$_j$ (not shown, see e.g., FIG. 1) in distal support plate 130 and each second nut 211 being rotatably coupled to corresponding j$^{th}$ aperture in proximal support plate 140, whereby rotation of first nut 210 through distal support plate 130 a predetermined number of degrees (e.g., about 180°) selectively causes holder 250 to engage or disengage actuator 300.

As further illustrated in FIG. 8, device or apparatus 10 can further have plurality of substantially elongated members or probes 200$_m$ having a predetermined function, each m$^{th}$ probe 200$_m$ operably coupled to bore 230, extending beyond distal end support plate 130, as well as proximal support plate 140, through aperture 240 disposed on proximal support plate 140, aligned with holder's 250 bore 252 and through channels 515 disposed in orifice 510 of housing base 500 and through apertures defined in insert 550.

In an embodiment, provided herein is a drive device for contacting at least one probe with a biological tissue sample, the device comprising at least one holder operably coupled to at least one probe having a predetermined function; at least one selector configured to selectively and reversibly couple and/or decouple said at least one holder to, and/or from an actuator independently, wherein, said actuator is configured for controllably and concurrently move any coupled holder, wherein (i) the actuator is a screw gear, (ii) the actuator is an internally threaded sleeve, (iii) the selector is capable of selectively coupling and/or decoupling the holder to and/or from the actuator at any position along a longitudinal axis length, wherein (iv) wherein the at least one holder further comprises an engaging holder member adapted to engage the actuator, slidably coupled to a stationary holder member incapable of engaging the actuator, the engaging holder member defining a support rod bore therein having an oval cross section, the stationary holder member configured to be radially immobile (in other words, stationary, incapable of moving along the X axis), (v) the holder further comprises a tuning member, adapted to provide incremental axial motion upon rotation of the actuator operably coupled to the upper holder member, wherein (vi) the predetermined function is data collection, stimulation, sensing, drug delivering or a combination comprising one or more of the foregoing, (vii) wherein the selector is rotated 180 degrees to couple, decouple or both, the holder to and/or from the actuator, wherein (viii) the actuator, (ix) the engaging holder member, (x) the tuning member or any combination of the actuator, engaging holder member, or tuning member is motorized, wherein (xi) the biological sample is an animal's organ, a tissue sample, a slide, cerebral-spinal fluid, a neuron, or brain tissue, (xii) the predetermined function is data collection, stimulation, sensing, drug delivering or a combination comprising one or more of the foregoing, and wherein the device (xiii) comprises between 2 and about 256 holders.

In another embodiment, provided herein is a method for contacting at least one probe with a biological tissue sample comprising exposing the biological tissue sample; providing a device comprising: at least one holder operably coupled to at least one probe having a predetermined function; and at least one selector configured to selectively and reversibly couple and/or decouple said at least one holder to, and/or from an actuator independently, wherein, said actuator is configured for controllably and concurrently move any coupled holder; positioning the device such that the probe will contact an area of interest in the biological tissue sample; coupling at least one probe to the actuator; activating the actuator, contacting the biological sample; and decoupling the at least one probe from the actuator, wherein (xiv) the actuator is a screw gear, or a threaded sleeve, (xv) the selector is capable of selectively coupling and/or decoupling the holder to and/or from the actuator at any position along a longitudinal axis length, (xvi) the at least one holder further comprises an engaging holder member adapted to engage the actuator, slidably coupled to a stationary holder member incapable of engaging the actuator and optionally a tuning member coupled to the engaging holder member, whereby the engaging holder member defining a support rod bore therein having an oval cross section, the stationary holder member configured to be radially immobile, wherein (xvii) the probe is a cannula, an electrode, a tetrode, a needle, a sensor, fiber optic, fiber-optogenic (FOG) stimulator, a pipette, or a combination comprising one or more of the foregoing, and wherein (xviii) the predetermined function is data collection, stimulation, sensing, drug delivering or a combination comprising one or more of the foregoing.

One or more components may be referred to herein as "configured to," "configured by," "configurable to," "operable/operative to," "adapted/adaptable," "able to," "conformable/conformed to," etc. The terms (e.g. "configured to") can generally encompass active-state components and/or inactive-state components and/or standby-state components, unless context requires otherwise.

While in the foregoing specification the selectively and concurrently implementable multi-probe microdrive apparatus has been described in relation to certain preferred embodiments, and many details are set forth for purpose of illustration, it will be apparent to those skilled in the art that the disclosure of the selectively and concurrently implementable multi-probe microdrive apparatus is susceptible to additional embodiments and that certain of the details described in this specification and as are more fully delineated in the following claims can be varied considerably without departing from the basic principles of this invention.

I claim:

1. A drive device for contacting a plurality of probes with a biological tissue sample, the device comprising:
   a. a plurality of holders, each holder operably coupled to at least one probe having a predetermined function; and
   b. a plurality of selectors, each selector coupled to one of the holders, configured to selectively and reversibly couple and/or decouple the holder to, and/or from a single actuator independently, wherein, the single in actuator is configured for controllably and concurrently move two or more holders coupled to the single actuator along the single actuator's longitudinal axis.

2. The device of claim 1, wherein the single actuator is a screw gear.

3. The device of claim 1, wherein the single actuator is an internally threaded sleeve.

4. The device of claim 1, wherein each selector is capable of selectively coupling and/or decoupling each holder to which each selector is coupled to and/or from the single actuator at any position along a longitudinal axis length of the single actuator.

5. The device of claim 1, wherein each holder further comprises:

an engaging holder member adapted to engage the single actuator, slidably coupled to a stationary holder member incapable of engaging the single actuator, the engaging holder member defining a support rod bore therein having an oval cross section, the stationary holder member configured to be radially immobile.

6. The device of claim 5, wherein each holder further comprises a tuning member, adapted to provide incremental axial motion upon rotation of the single actuator operably coupled to engaging holder member.

7. The device of claim 6, wherein the tuning member is motorized.

8. The device of claim 5, wherein the engaging holder member is motorized.

9. The device of claim 1, wherein the at least one probe is a cannula, an electrode, a tetrode, a needle, a sensor, fiber optic, optogenetic stimulator, a pipette, or a combination comprising one or more of the foregoing.

10. The device of claim 9, wherein the predetermined function is data collection, stimulation, sensing, drug delivering or a combination comprising one or more of the foregoing.

11. The device of claim 10, wherein the biological sample is an animal's organ, a tissue sample, a slide, cerebral-spinal fluid, a neuron, or brain tissue.

12. The device of claim 1, wherein each selector is rotated 180 degrees to couple and/or decouple each holder to which the selector is coupled to and/or from the single actuator.

13. The device of claim 1, wherein the single actuator is motorized.

14. The device of claim 1, comprising between 2 and 256 holders.

15. A method for contacting a plurality of probes with a biological tissue sample comprising:
   a. exposing the biological tissue sample;
   b. providing a device comprising:
      i. a plurality of holders, each holder operably coupled to at least one probe having a predetermined function; and
      ii. a plurality of selectors, each selector coupled to one of the holders, configured to selectively and reversibly couple and/or decouple the holder to, and/or from a single actuator independently, wherein, said actuator is configured for controllably and concurrently move two or more coupled holders along the single actuator's longitudinal axis;
   c. positioning the device such that two or more probes of the holders coupled to the single actuator will contact an area of interest in the biological tissue sample;
   d. coupling at least two holders to the single actuator;
   e. activating the single actuator;
   f. contacting the biological sample; and
   g. decoupling at least two holders from the single actuator.

16. The method of claim 15, wherein the single actuator is a screw gear, or a threaded sleeve.

17. The method of claim 15 or 16, wherein each selector is capable of selectively coupling and/or decoupling each holder to which each selector is coupled, to and/or from the single actuator at any position along a longitudinal axis length of the single actuator.

18. The method of claim 15, wherein each holder further comprises an engaging holder member adapted to engage the single actuator, slidably coupled to a stationary holder member incapable of engaging the single actuator and optionally a tuning member coupled to the engaging holder member, whereby the engaging holder member defining a support rod bore therein having an oval cross section, the stationary holder member configured to be radially immobile.

19. The method of claim 15, wherein the at least one probe is a cannula, an electrode, a tetrode, a needle, a sensor, fiber optic, optogenetic stimulator, a pipette, or a combination comprising one or more of the foregoing.

20. The method of claim 19, wherein the predetermined function is data collection, stimulation, sensing, drug delivering or a combination comprising one or more of the foregoing.

* * * * *